(12) United States Patent
Keener

(10) Patent No.: US 9,925,351 B2
(45) Date of Patent: Mar. 27, 2018

(54) AROMATHERAPY DEVICE

(71) Applicant: Jennifer K. Keener, Massillon, OH (US)

(72) Inventor: Jennifer K. Keener, Massillon, OH (US)

(*) Notice: Subject to any disclaimer, the term of this patent is extended or adjusted under 35 U.S.C. 154(b) by 215 days.

(21) Appl. No.: 14/748,352

(22) Filed: Jun. 24, 2015

(65) Prior Publication Data

US 2016/0001035 A1   Jan. 7, 2016

Related U.S. Application Data

(60) Provisional application No. 62/019,612, filed on Jul. 1, 2014.

(51) Int. Cl.
| | |
|---|---|
| *A61M 15/08* | (2006.01) |
| *A61L 9/12* | (2006.01) |
| *A61M 21/02* | (2006.01) |
| *B65D 71/06* | (2006.01) |
| *A61L 9/14* | (2006.01) |
| *A61M 11/04* | (2006.01) |
| *A61B 50/30* | (2016.01) |
| *A61M 21/00* | (2006.01) |

(52) U.S. Cl.
CPC ............ *A61M 21/02* (2013.01); *A61B 50/30* (2016.02); *A61L 9/14* (2013.01); *A61M 11/042* (2014.02); *A61M 15/08* (2013.01); *A61M 21/00* (2013.01); *B65D 71/06* (2013.01); *A61B 2050/3008* (2016.02); *A61M 2021/0016* (2013.01); *A61M 2205/3368* (2013.01); *A61M 2205/3653* (2013.01); *A61M 2205/8206* (2013.01); *A61M 2209/06* (2013.01)

(58) Field of Classification Search
CPC .... A61M 21/02; A61M 11/042; A61M 15/08; A61M 2021/0016; A61M 15/0028; A61M 15/0021; A61M 15/0065; A61L 9/14; A61L 2209/133
USPC ..... 239/308, 57, 34, 36, 38, 40; 128/200.19, 128/203.22; 206/568; 392/392; 428/905
See application file for complete search history.

(56) References Cited

U.S. PATENT DOCUMENTS

| | | | | |
|---|---|---|---|---|
| 168,972 A | * | 10/1875 | Dayton ..................... | A61L 9/12 128/207.14 |
| 2,620,228 A | * | 12/1952 | Howard .................... | B65F 7/00 220/87.1 |
| 3,087,679 A | * | 4/1963 | Wilson ................... | A01M 1/205 206/213.1 |
| 4,544,592 A | * | 10/1985 | Spector ..................... | A61L 9/03 239/56 |
| 4,890,791 A | * | 1/1990 | Hoffman ................. | A61L 9/127 239/326 |
| 4,955,945 A | * | 9/1990 | Weick ....................... | A61L 9/12 128/203.12 |

(Continued)

*Primary Examiner* — Arthur O Hall
*Assistant Examiner* — Joseph A Greenlund
(74) *Attorney, Agent, or Firm* — Sand & Sebolt; Howard L. Wernow

(57) ABSTRACT

An aromatherapy device includes a housing forming two annular wells for retaining a scented fluid therein. Each well includes an insert positioned in the well to assist the retention of the fluid in the well by providing a second contact surface for the fluid to contact. The shape of the annular well and the viscosity of the fluid discourage the fluid from leaking out of the housing if laid on its side.

17 Claims, 4 Drawing Sheets

(56) References Cited

U.S. PATENT DOCUMENTS

| | | | | |
|---|---|---|---|---|
| 5,121,881 | A * | 6/1992 | Lembeck | A61L 9/127 239/34 |
| 5,943,816 | A * | 8/1999 | Hyatt | A01M 1/2005 239/34 |
| 6,126,632 | A * | 10/2000 | Verbovszky | A47G 19/2266 220/712 |
| 6,557,375 | B1 * | 5/2003 | Simmons | A44C 15/002 63/1.11 |
| 7,841,337 | B2 * | 11/2010 | Djupesland | A61M 15/0091 128/200.23 |
| 8,662,409 | B2 * | 3/2014 | Tasz | A61L 9/048 239/303 |
| 8,677,679 | B2 * | 3/2014 | Black | A01M 1/2033 239/44 |
| 9,192,691 | B2 * | 11/2015 | Bourne | A61L 9/125 |
| 9,554,595 | B2 * | 1/2017 | Buchberger | A61M 15/06 |
| 2006/0196966 | A1 * | 9/2006 | Cheng | A47G 19/2205 239/60 |
| 2008/0190935 | A1 * | 8/2008 | Pankhurst | A61L 9/02 220/553 |
| 2010/0199984 | A1 * | 8/2010 | Williams, III | A61M 15/0065 128/200.23 |
| 2011/0011947 | A1 * | 1/2011 | Wallis | A61L 9/012 239/34 |
| 2014/0112649 | A1 * | 4/2014 | Irvin | A61L 9/03 392/390 |
| 2015/0053201 | A1 * | 2/2015 | Djupesland | A61M 11/006 128/200.23 |
| 2016/0001035 | A1 * | 1/2016 | Keener | A61M 15/08 206/568 |

\* cited by examiner

AROMATHERAPY DEVICE

CROSS REFERENCE TO RELATED APPLICATION

This application claims the benefit of U.S. Provisional Application Ser. No. 62/019,612, filed on Jul. 1, 2014; the disclosure of which is entirely incorporated herein by reference.

BACKGROUND

Technical Field

The present disclosure relates generally to the field of aromatherapy devices. More particularly, the present invention relates to aromatherapy devices including a scented fluid. Specifically, the present invention relates to a housing forming a well filled with scented fluid configured to prevent the fluid from leaking out of the housing.

Background Information

Aromatherapy is a form of treatment for certain ailments utilizing scented fluids or compounds. The scents are inhaled and a reaction occurs in the human brain to alter the user's mind, mood, cognitive abilities, or health. Some exemplary fluids often utilized in aromatherapy include essential oils, absolute oils, and carrier oils, amongst others.

One exemplary treatment which aromatherapy is used in is the cessation of cigarette smoking. When a person attempts to quit smoking cigarettes, they often have side effects such as increased hunger, which can lead to weight gain. Some aromatherapy treatments are used to reduce hunger cravings as a person weans their body from its nicotine addiction.

Recently, electronic cigarettes have begun using essential oils in their vaporizers to flavor-infuse vapor as a replacement to conventional cigarettes. The fluid for electronic cigarettes is readily available in the commercial market in a wide variety of flavors/scents and quantities.

SUMMARY

Issues continue to exist with current aromatherapy devices with the delivery of scents to a user, namely problems exist with fluid leaking out from some aromatherapy containers. Further, the electronic cigarette market keeps advancing the development of the scented fluids for use in electronic cigarettes. A need exists for an aromatherapy device configured to utilize the advantages of the wide variety of essential oils available for electronic cigarettes. The present invention addresses these and other issues.

In one aspect, an embodiment may provide an aromatherapy device comprising: a housing; a first cylinder having an inner surface, the first cylinder defining a portion of the housing; an first insert having an outer surface, the first insert smaller than the first cylinder and positioned radially inward from the inner surface; and a first aromatic fluid well formed between the inner surface of the first cylinder and the outer surface of the first insert configured to retain a scented fluid therein, wherein aroma associated with the fluid is inhaled by a user.

In another aspect, an embodiment may provide, an aromatherapy method comprising the steps of: providing a housing including a first member having an inner surface, an first insert smaller than the first member and positioned inward from the inner surface, the first insert having an outer surface, and a first aromatic fluid well formed between the inner surface of the first member and the outer surface of the first insert; filling the aromatic fluid well with a scented fluid; and positioning the housing beneath the nostrils of a user, wherein scent from the scented fluid is sensed by a user.

In yet another aspect, an embodiment may provide an aromatherapy kit comprising: a plurality of housings for retaining a scented fluid, wherein each housing includes: a first member having an inner surface; an first insert smaller than the first member and positioned radially inward from the inner surface, the first insert having an outer surface; and a first aromatic fluid well formed between the inner surface of the first member and the outer surface of the first insert configured to retain a scented fluid therein, wherein aroma associated with the fluid is sensed by a user; and a case including a plurality of retaining areas, each one of the plurality of retaining areas shaped complementary to each one of the plurality of housings, and one housing stored in one retaining area when the housing is not in use.

In one aspect, an embodiment may provide an aromatherapy device comprising: a cylindrical housing; an insert in the housing; and an aroma fluid well formed between the cylindrical housing and the insert configured to retain a scented fluid therein for inhalation of a scent by a user.

In another aspect, an embodiment may provide an aromatherapy device comprising: a scented fluid in a well formed in a housing device; and a mouthpiece coupled to the housing device positioning the fluid near a nostril of a user for inhalation of the scent.

In another aspect, an embodiment may provide an aromatherapy kit comprising: a plurality of aroma fluid containing housings; and a case including a plurality retaining areas shaped complementary to the housings for retaining the housings in the retaining areas.

In another aspect, an embodiment may provide an aromatherapy device including a housing forming two annular wells for retaining a scented fluid therein. Each well includes an insert positioned in the well to assist the retention of the fluid in the well by providing a second contact surface for the fluid to contact. The shape of the annular well and the viscosity of the fluid discourage the fluid from leaking out of the housing if laid on its side.

BRIEF DESCRIPTION OF THE SEVERAL VIEWS OF THE DRAWINGS

A sample embodiment of the invention, illustrative of the best mode in which Applicant contemplates applying the principles, is set forth in the following description, is shown in the drawings and is particularly and distinctly pointed out and set forth in the appended claims. The accompanying drawings, which are incorporated in and constitute a part of the specification, illustrate various example methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

Similar numbers refer to similar parts throughout the drawings.

DETAILED DESCRIPTION

Figure 4:
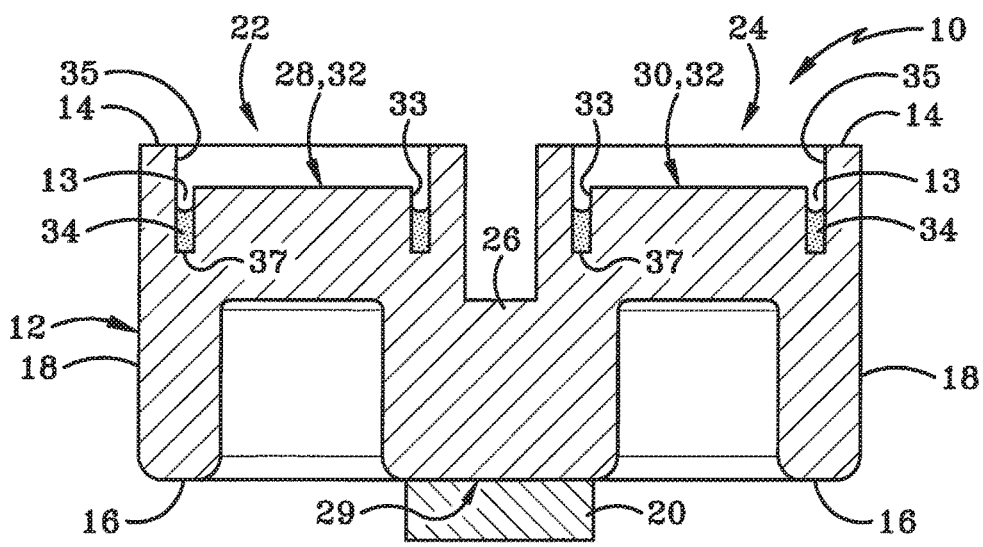
FIG. 4 is a cross-section view of the aromatherapy device taken along line 4-4 in FIG. 3.
Figure 5:
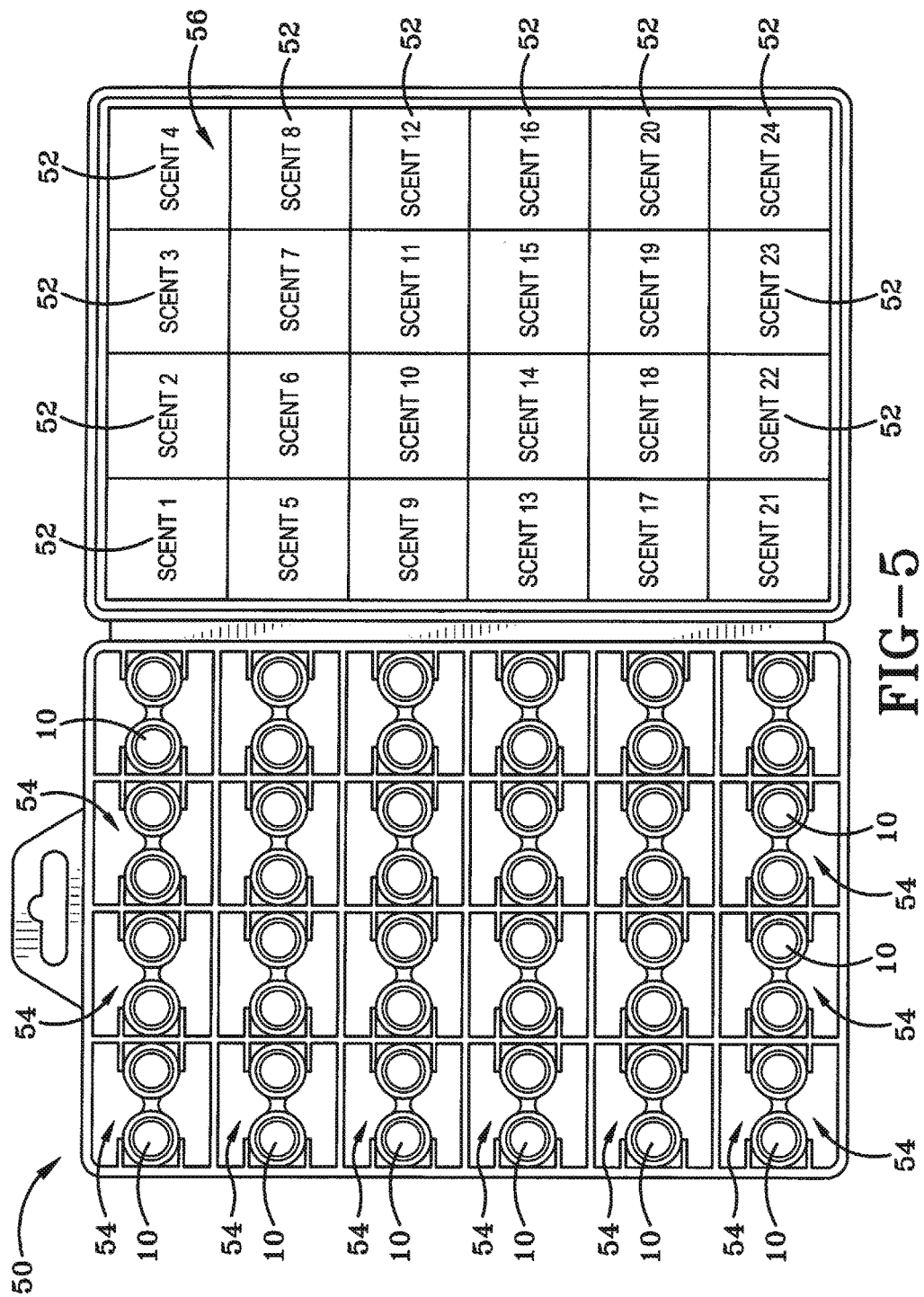
FIG. 5 is a top view of the aromatherapy device shown in a kit with a plurality of aromatherapy devices, each containing a different scent.
Figure 6:
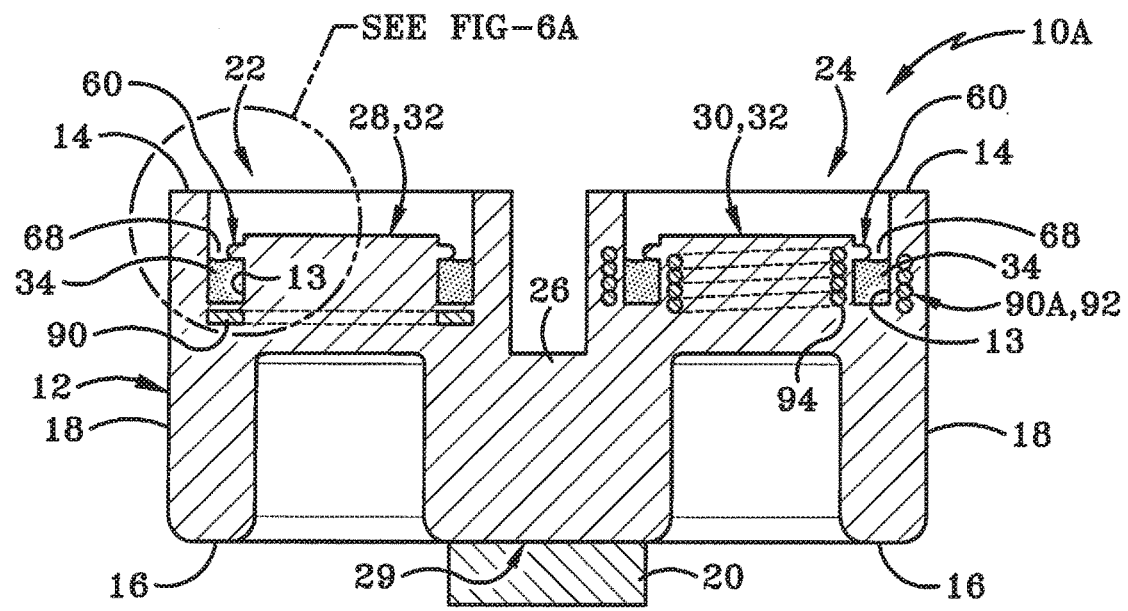
FIG. 6 is a cross-section view of the an additional embodiment of an aromatherapy device including a lip disposed in a well taken along line 4-4 in FIG. 3.
Figure 6A:
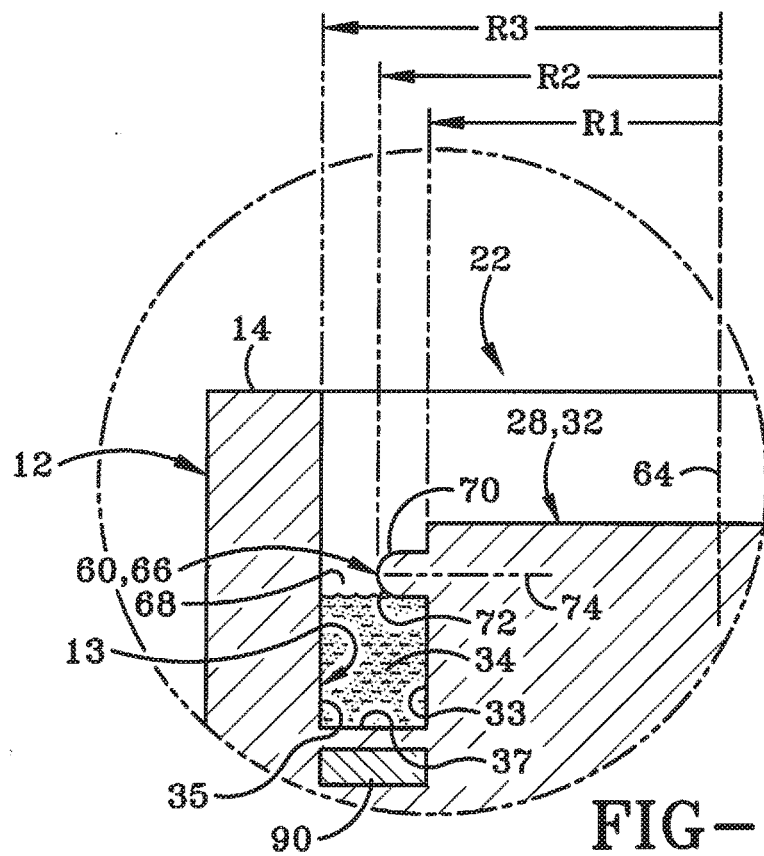
FIG. 6A is an enlarged view of the area identified in FIG. 6.

The aromatherapy device of the present invention is depicted throughout FIGS. 1-5, generally as reference numeral 10; and depicted in FIG. 6 and FIG. 6A as reference numeral 10A. Devices 10 and 10A include a housing 12 forming a pair of annular wells 13 (FIG. 3) therein for retaining an aromatherapy fluid 34 having a scent.

Figure 1:
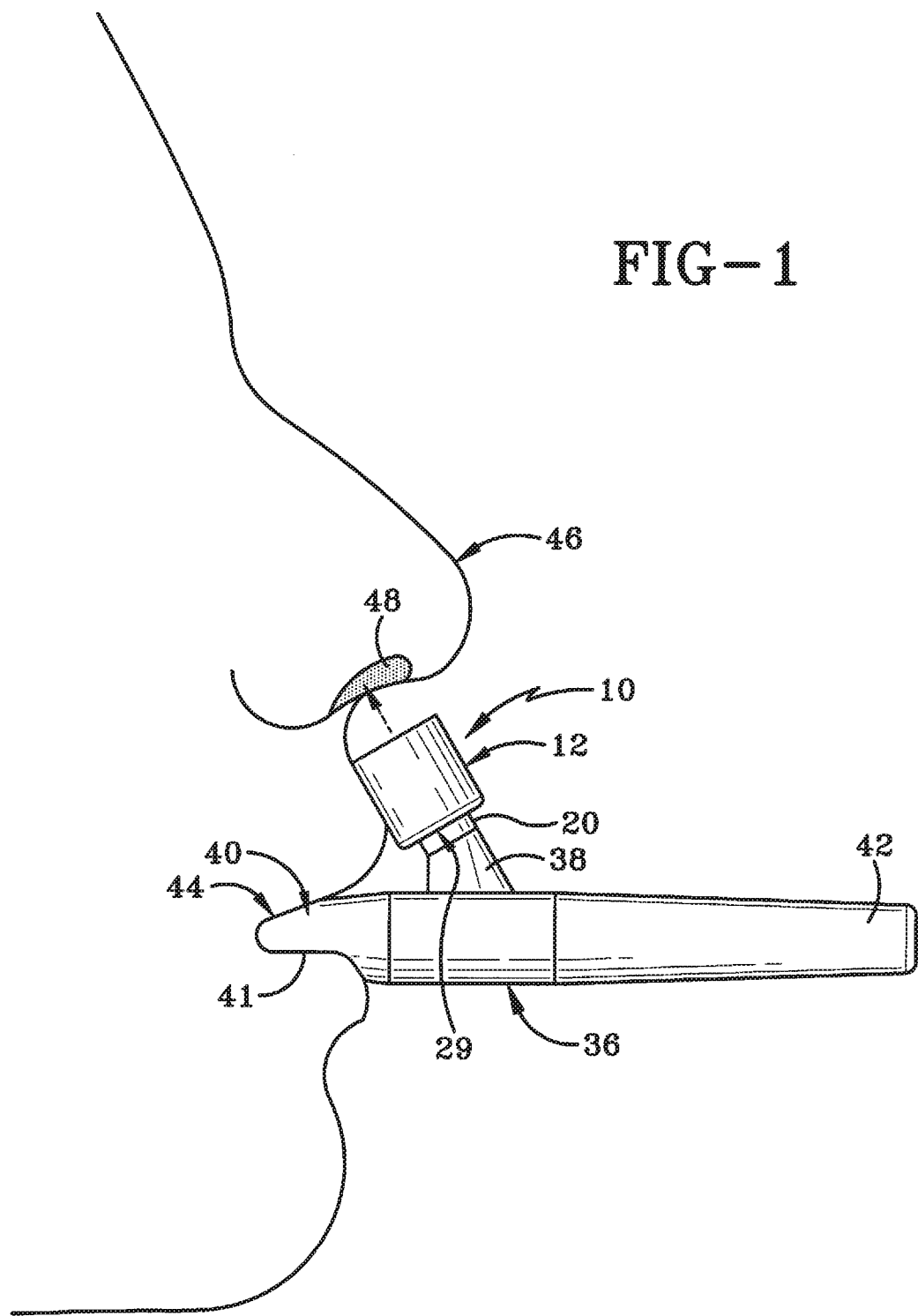
FIG. 1 is an environmental side view of the aromatherapy device of the present invention shown attached to a mouthpiece and aromas being inhaled from the aromatherapy device.
Figure 2:
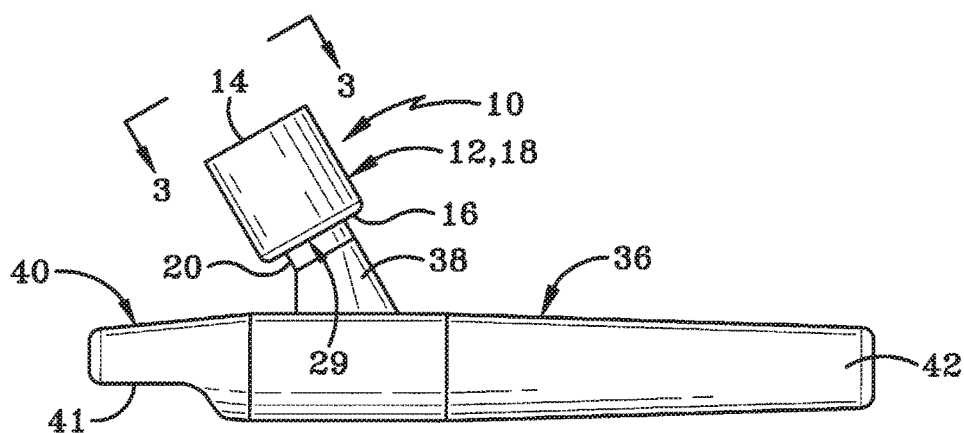
FIG. 2 is a side view of the aromatherapy device attached to the mouthpiece.

As depicted in FIG. 1 and FIG. 2, aromatherapy device 10 (or device 10A) is configured to attach a mouthpiece 36 via a connecting member 38 adjacent the attachment base 29 of housing 12. In the shown embodiment, the connecting member 38 is a magnet to connect device 10 to mouthpiece 36, however other conventional manners of mechanical, chemical, or non-mechanical and non-chemical securements in which an aromatherapy device may be coupled to a mouthpiece or handle as understood in the art are entirely possible. In one particular embodiment, connecting member 38 provides an angled connection between the housing 12 and the mouthpiece 36, wherein when the housing 12 and mouth piece 36 are connected by the angled connection, the first top surface 14 of the first cylinder is not facing directly vertical, and a limiting member (i.e., lip 60) discourages the fluid 34 from flowing out of the well 13.

Mouthpiece 36 includes a first end 40 for inserting into user's mouth 44 and a second end 42 spaced opposite therefrom for gripping with the user's hand. When the mouthpiece 36 is inserted into the user's mouth 44, device 10 (or device 10A) is aligned with the user's nose 46. In one particular embodiment, left and right annular wells 13 (introduced below) are each respectively aligned with the left and right nostril 48 of the user, maximizing the amount of scent sent by the operator during inhalation. Additionally, while reference is made to inserting an end of mouthpiece 36 into a user's mouth 44, some embodiments of mouthpiece 36 may include a recession 41 shaped complementary to a user's lip to rest thereon when in use.

Figure 3:
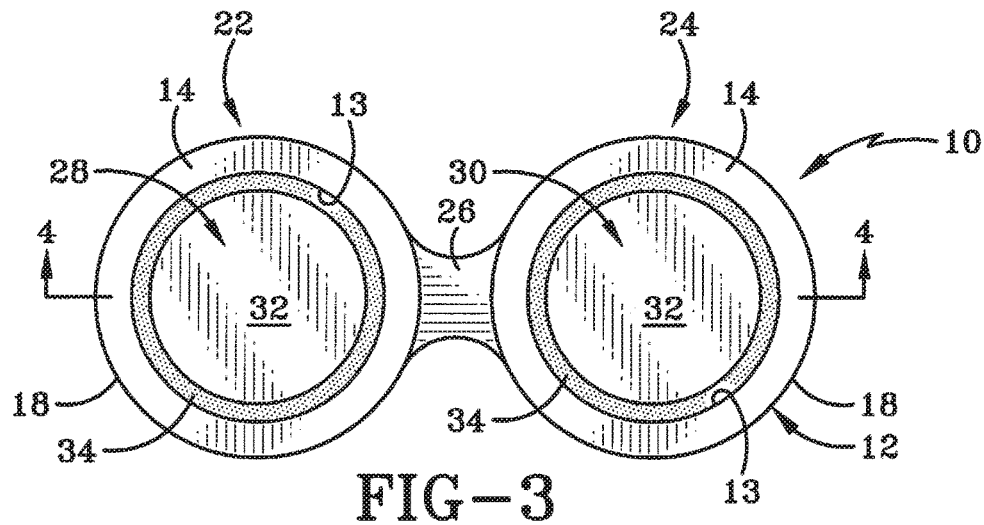
FIG. 3 is a top view of the aromatherapy device taken along line 3-3 in FIG. 2.

As detailed in FIGS. 2-4, housing 12 includes an upwardly facing top surface 14 spaced apart from a downwardly facing bottom surface 16 and a sidewall 18 extending therebetween. Sidewall 18 is substantially continuous and curvilinear having a generally figure-eight-like configuration when viewed from above (FIG. 3). Housing 12 further includes an attachment member 20 near a base 29 on or adjacent the bottom surface 16.

Each annular well 13 is formed in respective left and right end cylinders 22, 24 of the figure eight housing 12. Left and right cylinders 22, 24 are connected to each other via a middle connection member 26. A first insert 28 and a second insert 30, each including an annular outer surface 33, respectively bounds a portion of each annular well 13. An inner surface 35 on each left and right cylinder 22, 24 bounds annular well 13 opposite annular surface 33. Annular surface 33 faces inner surface 35 when viewed in cross section.

With primary reference to FIG. 4, first and second inserts 28, 30 have a top surface 32 lower than the top surface 14 of housing 12 which is configured to act as a retaining edge for the aroma fluid filled within each well. One non-limiting advantage of the inserts 28, 30 is that it retains a viscous scented fluid 34 in the well by providing another surface for the viscous fluid 34 to contact.

Well 13 has a depth measured from top surface 32 to a well bottom 37. In one embodiment, the well depth may be in a range from about 1, 2, or 3 millimeter (mm) to about 9, 10, or 11 mm. Further, in device 10, well 13 has a uniform width in cross section. Stated otherwise, the width of well 13 is the same at the top of the well as it is near the bottom of the well. The width of well 13 measured from annular surface 33 to inner surface 25 may be in a range from about 0.1, 0.25, or 0.5 mm to about 1, 2, or 3 mm.

With reference to the viscous aromatherapy fluid 34 retained in annular wells 13 on device 10, one exemplary non-limiting aroma fluid 34 is commercially available as an E-Liquid for electronic cigarettes for sale by Vapor4Life Inc. of 4100 Commercial Ave, Northbrook, Ill. 60062. In one particular embodiment, fluid 34 contains an amount of glycerin, propylene glycol, or mixture thereof to create a viscosity that discourages the fluid 34 from leaving the well 13 or flowing out of the well 13 under gravitational forces even when housing 12 is resting along the sidewall 18 on its side. In one particular embodiment, fluid 34 may be a non-Newtonian fluid.

Fluid 34 may be fabricated to include various scents from scent additives. Some non-limiting exemplary scents associated with viscous fluid 34 are chocolate peppermint, peanut butter cup, pancake, waffle, clove, chocolate, vanilla, cinnamon roll, caramel, English toffee, Choco-caramel peanut, peppermint ice cream, milk chocolate macadamia nut, white chocolate, blueberry/peach cobbler, chocolate-covered banana, almond coconut, coffee, expresso coffee, caramel mocha frappe, café mocha, vanilla mocha frappe, cappuccino, vanilla shake, champagne, java mint, rum and cola, Irish cream, energy drink, blueberry, peach, grape, cherry, regular tobacco, menthol tobacco, pipe tobacco, and cigar tobacco.

Scented fluid 34 provides an aroma-based therapeutic effect when the aroma associated with scented fluid 34 is inhaled by a user. In another particular example, fluid 34 to be inhaled may have cognitive altering abilities, such as to relieve stress and improving the mood of the user.

As depicted in FIG. 5, in one particular embodiment of the present invention, device 10 or device 10A is supplied as part of a kit 50 with a plurality of scents 52, each distinct from the other scents (exemplary scents provided above) for home use, enabling a user to sense a wide variety of smells. The kit 50 includes a plurality of device retention areas 54 configured to securely store a plurality of devices 10 or a plurality of devices 10A in a safe environment. The kit 50 may retain the devices 10, 10A in a manner such that the top surface 14 of housing 12 faces upward, or alternatively, kit 50 may store devices 10, 10A on their side. In each configuration, aroma fluid 34 should not leak out from the top of the annular well 13. In accordance with one particular embodiment of the present invention, housing 12 is constructed from a durable material, such as metal or a polymer that is resistant to breakdown from any chemicals residing in the fluid. Further, kit 50 includes an index 56 on the inside lid to assist a user in locating a specific scent pre-loaded in a corresponding housing. While FIG. 5 depicts a total of twenty four non-limiting scents, clearly there may be a different number of scents depending on the size of the kit.

In one exemplary embodiment, aromatherapy kit 50 comprises: a plurality of devices 10 for retaining a scented fluid, wherein each device 10 includes: a first member having an inner surface 35; an first insert 28 smaller than the first member and positioned radially inward from the inner surface 35, the first insert 28 having an outer surface 33; and a first aromatic fluid well 13 formed between the inner surface 35 of the first member and the outer surface 33 of the first insert configured to retain a scented fluid 34 therein, wherein aroma associated with the fluid is sensed by a user; and a case including a plurality of retaining areas 54, each one of the plurality of retaining areas 54 shaped complementary to each one of the plurality of devices 10, and one device 10 stored in one retaining area 54 when the device 10 is not in use. In kit 50, the scented fluid 34 includes scent additives and additionally comprises one or more of the following: (i) glycerin, (ii) propylene glycol, and (iii) a mixture of glycerin and propylene glycol.

As depicted in FIG. 6 and FIG. 6A, device 10A includes a lip 60 extending radially outward from annular surface 33 relative to vertical centerline extending through the center of one of the inserts. Here, centerline 64 is shown with reference to insert 28.

A first radius distance R1 of insert 28 is measured from centerline 64 to annular surface 33. A second radius distance R2 is measured from centerline 64 to a terminal lip end 66 of lip 60. A third radius R3 is measured from centerline 64 to inner surface 35. The lip 60 extends radially outward from the annular surface 33 on the insert 28 and terminating at a lip end 66 radially inward relative to the inner surface 35 of the cylindrical housing. Lip 60 includes an upwardly facing convex surface 70 above an imaginary horizontal midline 74 and a downwardly facing convex surface 72 below the midline 74 when viewed in cross section.

A first neck 68 is defined between terminal lip end 66 and inner surface 25 on cylindrical housing 12. The width of first neck 68 is less than that of well 13 measured between annular surface 33 and inner surface 35 below lip 60. This provides an advantage of a narrow passageway to discourage scented fluid 34 from flowing out of well 13 in the event device 10, 10A is placed on its side. Additionally a second neck exists in second cylinder 24 similar to the first neck 68 described above.

In one particular embodiment, the width of first neck 68 is in a range from about 0.01, 0.025, or 0.1 mm to about 0.1, 0.25, 0.5, 1, or 2 mm. While well 13 has a width from about 0.1, 0.25, or 0.5 mm to about 1, 2, or 3 mm. In one particular embodiment, first neck 68 has a width that is half the width of well 13 measured between annular surface 33 and inner surface 35 below lip 60.

Device 10A may further include a heating element 90. Heating element 90 may be battery powered and be rechargeable utilizing battery technology currently available in other e-cigarettes or fluid vaporizers. In one particular embodiment, heating element 90 is an electric-resistive heater positioned within the body of each one of the cylinders 22, 24. FIG. 6 depicts heating element 90 entirely beneath the well 13 (when viewed in cross section) within cylinder 22 and heats the aromatic fluid 34 from below. However, it is entirely possible to have a resistive heating element 90A that extends vertically upward from the bottom of well 13 within the body of cylinders 22, 24. For example, a coil resistive heating element 90A is shown and including an outer coil 92 and an inner coil 94 would around the walls defining well 13, wherein outer coil 92 is radially outward of well 13 relative to center 64 and inner coil 94 is inward of well 13 relative to center 64. Either one of the heating elements 90 or 90A are advantageous to device(s) 10, 10A because heating up the walls defining well 13 to thereby impart heat to fluid 34 makes the aroma/scent associated with said fluid richer/stronger than the fluid would be at room temperature.

In accordance with one aspect of the present invention, device 10, 10A releases therapeutic aromas or scents for inhalation by a user. The therapeutic aromas may have advantages and benefits such as reducing appetite as a person is attempting to quit smoking cigarettes, or such as encouraging the pleasant enjoyment of soothing aromas.

In operation, device(s) 10, 10A is provided to a user in a fully constructed form from a supplier in accordance with the embodiments described above. A user fills the annular well 13 with a scented fluid 34. One exemplary commercially available scented fluid 34 is available for sale ordinarily used in an electronic cigarette. The user grasps the housing 12 with the top surface 14 facing upwardly to expose the opening to the annular well 13. An amount of the scented fluid 34 is poured into the well 13. In one particular embodiment, the amount of fluid 34 in the well 13 does not rise above the top surface 32 of the insert 28, 30 when device 10 is placed with its top surface facing upwardly. Once well 13 is filled with fluid 34, the device 10 may be packed into a kit 50 for later use, or attached to the mouthpiece 36.

In operation and with respect to device 10A, once the well 13 is filled with fluid, the lip 60 limits and discourages fluid 34 from exiting well 13 in the event device 10A is laid on its side. The narrow neck 68 enables the surface tension of fluid 34 to remain high over the neck width as opposed to the amount of surface tension spanning the width of well 13 in device 10. The well 13 in device 10A has a non-uniform width inasmuch as the neck 68 is about half as wide and the well portion beneath lip 60.

In operation, once device 10 has been loaded or filled with fluid 34 in the non-limiting manner described above, device 10 is extracted from the retention area 54 in the kit container 50. The device 10 is then connected to the mouthpiece 36 via the magnet 38 to the bottom surface 16 on the mouthpiece 36. The first end 40 of mouthpiece 36 is moved towards the user's mouth 44 and nose 46. In one particular embodiment, the user places the first end 40 into their mouth 44.

With the first end 40 in the user's mouth 44, the device 10 is positioned slightly beneath the nostrils 48 at an angle complementary to the user's upper lip. The user then inhales through their mouth and nose simultaneously, or at least as simultaneously as possible, to get the full effect of the scent. Stated otherwise, the scent of the fluid affects the human sense of smell stronger when a person tries to inhale through their mouth and nose at the same time.

In some instances, the user may turn on heating element 90 or 90A to warm the aromatic fluid 34 prior to inhalation. The warming of fluid 34 create a stronger scent than if the fluid was placed in device 10 (or device 10A) at room temperature. Preferably, heating element 90 or 90A may be coupled to temperature control logic to regulate the temperature to which fluid 34 is heated. The purpose of the control logic is ensure the fluid is not heated beyond its boiling point which would lead to the fluid evaporating from the well 13. "Logic", as used herein, includes but is not limited to hardware, firmware, software and/or combinations of each to perform a function(s) or an action(s), and/or to cause a function or action from another logic, method, and/or system. For example, based on a desired application or needs, the temperature control logic may include a software controlled microprocessor, discrete logic like a processor (e.g., microprocessor), an application specific integrated circuit (ASIC), a programmed logic device, a memory device containing instructions, an electric device having a memory, or the like. The temperature control logic may include one or more gates, combinations of gates, or other circuit components. The logic may also be fully embodied as software. Where multiple logics are described, it may be possible to incorporate the multiple logics into one physical logic. Similarly, where a single logic is described, it may be possible to distribute that single logic between multiple physical logics.

After usage, device 10 is placed back into the respective compartment in kit 50. Another advantage of device 10 filled with fluid 34 is that fluid 34 will not leak out the top of device 10 if placed on its side. When device 10 is laid on its side, fluid 34 may extend beyond top of surface 32 of the insert 28, 30 due to gravitational forces, but fluid 34 will not leak out and is contained by the edge of top surface 14.

One exemplary method of use of device 10 or 10A may include the steps of: providing a housing 12 including a first member (i.e., first cylinder 22) having an inner surface 35, an first insert 28 smaller than the first member and positioned inward from the inner surface 35, the first insert 28 having an outer surface 33, and a first aromatic fluid well 13 formed between the inner surface 35 of the first member and the outer surface 33 of the first insert 28; filling the aromatic fluid well 13 a scented fluid 34; and positioning the housing 12 beneath nostrils 48 on a user, wherein scent from the scented fluid 34 is sensed by a user. This method may further include the step of: discouraging the scented fluid 34 from flowing out of the fluid well 13 when the housing is positioned such that a top surface 14 of the first member is not facing directly vertical (FIG. 1 and FIG. 2). Wherein the step of discouraging may be accomplished by a lip 60 extending radially outward from the outer surface 33 of the first insert 28 towards the inner surface 35 of the first member and terminating at a lip end 66; wherein a neck section 68 is defined between the lip end 66 and the inner surface 35 of the first member, the neck section 68 having a width less than that of the aromatic fluid well. Further, this exemplary method may include wherein the step of positioning the housing beneath nostrils 48 is accomplished by attaching the housing 12 to a mouthpiece 36, selectively and repeatably, wherein the mouthpiece 36 is held in place by a user mouth 44.

Alternative embodiments of the present invention are also herein contemplated by way of non-limiting example. In one particular alternative embodiment, device 10 may be in fluid communication with a separate fluid source connected via tubing and a pump. The pump may be electronically controlled to initiate the flow of scented fluid 34 to device 10. The electronic control may include a bank of scented fluids 34 for the operator to choose from. There also may be a plurality of levers or valves to selectively open or close a desired scent 34 from a source in either a manual or electronic manner.

Another alternative embodiment may provide a device 10 retaining a scented fluid 34 mixed with a gel in the annular well. In this embodiment, scented fluid mixed with a pectin gel, similar to Sure-Jell® commercially available for sale by Kraft foods. The gel increases the viscosity of the mixture to ensure it remains in the annular well.

Another alternative embodiment of the present invention provides a housing 12 contained in the mouthpiece 36 for convenient travel. This alternative embodiment provides a hollow storage container within the body of the mouthpiece 36 that is selectively opened by a user to reveal the device stored inside. The user then connects the housing to the outside of mouthpiece 36 as shown in FIG. 1, and then the user may store the device 10 inside the mouthpiece 36 when finished.

Yet another alternative embodiment may include scented fluid 34 stored within a cavity inside mouthpiece 36. In this instance, tubing may exist to draw the stored fluid 34 to the annular wells 13 on device 10. Further, tubing may extend to the first end 40 of mouthpiece 36 so that the user may inhale simultaneously through the user's nose and mouth in accordance with the techniques described herein.

Another non-limiting alternative embodiment may include a tube bifurcating to create a generally Y-shaped member acting as the mouthpiece. Around the tube there may be layers of scents in compartments housed adjacent the tube. The tube may define a plurality of holes for attaching the scent compartments there around. Each scent compartment could have a small device 10 to keep the fluid 34 from leaking out. Each compartment may have a sliding door. Because the device 10 in this alternative embodiment may be smaller than in the embodiments described above, annular well 13 would contain about 1-3 drops of fluid 34. All of the sliding doors could be connected by a sturdy, thin cord so when a user pulls on a lever operatively connected to a desired scent located outside of the device 10, the cover then closes other doors so the other scents would be pulled tightly shut. Thus, in this embodiment there will be one scent door open all the time. The aroma from a scented fluid located adjacent an open door will enter into the aperture of the tube flowing upwardly to the generally Y-shaped mouth piece. Additionally, there may be an instance where two or more of these scent containers are open at a single time, allowing the aromas to mix in the container outside the device then collectively flow through the apertures at the lower end of the tube towards the Y-shaped mouthpiece.

Another non-limiting alternative embodiment may include a headset-like device electronically controlled by a remote control to change the scents. The headset is donned by a user such that it wraps around the user's head to free up the user's hands to perform another task. The headset may be configured with a device 10 retaining area positioned adjacent the user's nose when the headset is donned.

Top surface 32 is depicted throughout the figures as a flat horizontal surface when viewed in cross section, however it is possible that top surface 32 be arcuate, either convexly or concavely. Further, future embodiments may include a concave top surface bowing downwardly to define a second well radially inward (i.e., towards the center) relative to well 13. This may prove advantageous to mix scents without actually mixing fluids.

Further, for brevity, it is to be understood that the second cylinder 24 having second insert 30 includes the same features described above and reference numerals have similar meanings with respect to each left and right (first and second) cylinder 22, 24. Namely, devices 10 and 10A include a second cylinder having an inner surface, the second cylinder defining another portion of the housing; a second insert having an outer surface, the second insert smaller than the second cylinder and positioned radially inward from the inner surface; and a second aromatic fluid well formed between the inner surface of the second cylinder and the outer surface of the second insert configured to retain a scented fluid therein, wherein aroma associated with the fluid is inhaled by a user. The first cylinder 22 and the second cylinder 24 are linearly aligned for positioning directly beneath two nostrils of the user when viewed from above (FIG. 3).

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the preferred embodiment of the invention are an example and the invention is not limited to the exact details shown or described.

What is claimed:

1. An aromatherapy device comprising: a housing;
    a first cylinder formed from a portion of the housing, the first cylinder having an inner cylindrical surface and defining a portion of the housing; a first insert having an outer cylindrical surface;
    the first insert being smaller than the first cylinder and positioned radially inward from the inner cylindrical surface;
    a first aromatic fluid annular well formed between the inner cylindrical surface of the first cylinder and the outer cylindrical surface of the first insert adapted to retain a scented fluid therein, wherein aroma associated with the scented fluid is adapted to be inhaled by a user,
    a first top surface on the first cylinder;
    a second top surface on the first insert forming a peripheral edge for adapted to retain the scented fluid in the annular well below the first top surface; and wherein the second top surface is lower than the first top surface;
    a non-pivotable mouthpiece operatively coupled to the housing, and
    wherein the mouthpiece includes an elongated member having a proximal and distal end, such that the proximal end is adapted to be inserted into a mouth of a user and the housing is located at a proximal location with respect to the distal end, the top surface of the cylinder is adapted to be positioned outside and underneath a nostril of the user when the mouthpiece is inserted into the user's mouth.

2. The aromatherapy device of claim 1, further comprising: a lip extending radially outward from the outer cylindrical surface on the first insert and terminating at a lip end; and
    wherein the lip end is radially inward relative to the inner cylindrical surface of the first cylinder and a first neck defined between the lip end and the inner cylindrical surface of the first cylinder.

3. The aromatherapy device of claim 2, wherein the neck has a width less than that of the well.

4. The aromatherapy device of claim 2, wherein the lip includes an upwardly facing convex surface above an imaginary horizontal midline and a downwardly facing convex surface below the midline when viewed in cross section.

5. The aromatherapy device of claim 2, wherein the first aromatic fluid annular well has a non-uniform width when viewed in cross section.

6. The aromatherapy device of claim 1, further comprising: a well bottom that is annular in shape and positioned between the inner cylindrical surface of the first cylinder and the outer cylindrical surface of the first insert;
    a well depth measured from the second top surface on the first insert to the well bottom in a range from about 1 mm to about 11 mm.

7. The aromatherapy device of claim 1, wherein the housing and the mouthpiece are selectively and repeatably attachable and detachable relative to each other.

8. The aromatherapy device of claim 1, further comprising:
    an angled connection between the housing and the mouthpiece, wherein when the housing and mouth piece are connected by the angled connection, the first top surface of the first cylinder is not facing directly vertical, and
    a limiting member for discouraging the fluid from flowing out of the well.

9. The aromatherapy device of claim 1, further comprising:
    a second cylinder having an inner cylindrical surface, the second cylinder defining another portion of the housing;
    a second insert having an outer cylindrical surface, the second insert smaller than the second cylinder and positioned radially inward from the inner cylindrical surface; and
    a second aromatic fluid annular well formed between the inner cylindrical surface of the second cylinder and the outer cylindrical surface of the second insert adapted to retain a scented fluid therein, wherein aroma associated with the fluid is adapted to be inhaled by a user.

10. The aromatherapy device of claim 9, wherein the first cylinder and the second cylinder are linearly aligned for positioning directly beneath two nostrils of the user.

11. The aromatherapy device of claim 9, further comprising:
    a heating element carried by the first cylinder configured to heat the scented fluid.

12. The aromatherapy device of claim 1, wherein the first aromatic fluid annular well has a uniform width measured from the inner cylindrical surface of the first cylinder and the outer cylindrical surface of the first insert in a range from about 0.1 mm to about 3 mm.

13. The aromatherapy device of claim 1, wherein the first cylinder and the first insert are fixed so as to not rotate relative to each other.

14. The aromatherapy device of claim 1, wherein the first cylinder and the first insert are formed from one material.

15. The aromatherapy device of claim 1, wherein the first insert is formed from a non-absorptive durable material.

16. The aromatherapy device of claim 9, wherein the first cylinder and the second cylinder are oriented in a similar direction.

17. The aromatherapy device of claim 9, wherein the housing is shaped like a figure eight.

* * * * *